(12) United States Patent
Hefner et al.

(10) Patent No.: US 12,011,293 B2
(45) Date of Patent: *Jun. 18, 2024

(54) ENERGY MANAGEMENT BASED ON A CLOSED SWITCH CONFIGURATION

(71) Applicant: Medtronic MiniMed, Inc., Northridge, CA (US)

(72) Inventors: Jesse M. Hefner, Minneapolis, MN (US); Ellis Garai, Woodland Hills, CA (US); Al L. Mclevish, Roseville, MN (US); Brian J. Ferry, Saint Louis Park, MN (US); Philip R. Glassel, Stacy, MN (US); Paul W. Chevalier, Minnetonka, MN (US); David Y. Choy, San Gabriel, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/729,607

(22) Filed: Apr. 26, 2022

(65) Prior Publication Data

US 2023/0337984 A1    Oct. 26, 2023

(51) Int. Cl.
*A61B 5/145* (2006.01)
*A61B 5/00* (2006.01)
(Continued)

(52) U.S. Cl.
CPC .......... *A61B 5/6849* (2013.01); *H02J 7/0045* (2013.01); *H05K 5/0217* (2013.01);
(Continued)

(58) Field of Classification Search
CPC . A61B 5/14532; A61B 5/6833; A61B 5/6848; A61B 5/6849; A61B 5/688;
(Continued)

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

FOREIGN PATENT DOCUMENTS

| | | |
|---|---|---|
| WO | 2023211847 A1 | 11/2023 |
| WO | 2023211851 A1 | 11/2023 |

OTHER PUBLICATIONS

International Search Report and Written Opinion dated Aug. 7, 2023, in Application No. PCT/US2023/019649.

(Continued)

*Primary Examiner* — Levi Gannon

(74) *Attorney, Agent, or Firm* — Weaver Austin Villeneuve & Sampson LLP

(57) ABSTRACT

A sensor assembly for sensing a physiological characteristic includes a power source, a power control switch, and a power latch configured to latch an output of the power control switch. The sensor assembly also includes a power converter coupled to the power control switch. The power converter is configured to step down a voltage of the latched output of the power control switch for delivery of the latched output to one or more components of the sensor assembly. The power control switch is configured to inhibit consumption of power from the power source when the sensor assembly is in a pre-deployment state and output the latched output to the power converter in response to transition of the sensor assembly from the pre-deployment state to a deployed state.

20 Claims, 10 Drawing Sheets

(51) Int. Cl.
  *H01H 13/14* (2006.01)
  *H02J 7/00* (2006.01)
  *H05K 5/02* (2006.01)

(52) U.S. Cl.
  CPC ... *A61B 5/14532* (2013.01); *A61B 2560/0204* (2013.01); *A61B 2560/0209* (2013.01); *A61B 2560/063* (2013.01); *H01H 13/14* (2013.01); *H02J 2207/20* (2020.01)

(58) Field of Classification Search
  CPC .... A61B 2560/0204; A61B 2560/0209; A61B 2560/063; H01H 13/14; H02J 7/0045; H02J 2207/20; H05K 5/0217
  See application file for complete search history.

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | VanAntwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,672,328 B2 | 6/2017 | Saint et al. |
| 10,835,727 B2 | 11/2020 | Montalvo et al. |
| 2005/0003470 A1 | 1/2005 | Nelson et al. |
| 2007/0123819 A1 | 5/2007 | Mernoe et al. |
| 2009/0076336 A1* | 3/2009 | Mazar ............... A61B 5/318 |
| | | 600/300 |
| 2009/0209883 A1 | 8/2009 | Higgins et al. |
| 2010/0160861 A1 | 6/2010 | Causey, III et al. |
| 2010/0324392 A1 | 12/2010 | Yee et al. |
| 2015/0182153 A1* | 7/2015 | Feldman ............ A61B 5/7225 |
| | | 600/309 |
| 2016/0183794 A1 | 6/2016 | Gannon et al. |
| 2016/0183854 A1 | 6/2016 | Lee |
| 2020/0327973 A1 | 10/2020 | Pryor et al. |
| 2023/0345650 A1 | 10/2023 | Hefner et al. |

OTHER PUBLICATIONS

International Search Report and Written Opinion dated Aug. 7, 2023 in PCT Application No. PCT/US2023/019642.

* cited by examiner

ENERGY MANAGEMENT BASED ON A CLOSED SWITCH CONFIGURATION

TECHNICAL FIELD

This disclosure relates generally to medical devices, and more particularly, to energy management.

BACKGROUND

Sensor devices may be deployed in the treatment of or monitoring of various medical conditions. For example, a sensor device may be configured for use in obtaining an indication of glucose (e.g., interstitial glucose) levels and monitoring glucose levels in a diabetic person. In many cases, deployment of the sensor device involves coupling the sensor device to the skin of a person via an adhesive layer and using a sensor introducer to insert a sensor of the sensor device into subcutaneous tissue of the person. The sensor device typically includes a battery that serves to power the electrical components of the sensor device once the sensor device is deployed. However, it is desirable to minimize or avoid battery power consumption prior to deployment of the sensor device so as to maximize battery life and, thus, the operational life of the sensor device.

SUMMARY

This disclosure relates to energy management. Aspects of the disclosure relate to a sensor assembly for sensing a physiological characteristic of a user. The sensor assembly includes a power source, a power control switch, and a power latch configured to latch an output of the power control switch. The sensor assembly also includes a power converter coupled to the power control switch. The power converter is configured to step down a voltage of the latched output of the power control switch for delivery of the latched output to one or more components of the sensor assembly. The power control switch is configured to inhibit consumption of power from the power source when the sensor assembly is in a pre-deployment state and output the latched output to the power converter in response to transition of the sensor assembly from the pre-deployment state to a deployed state.

BRIEF DESCRIPTION OF THE DRAWINGS

The above and other aspects and features of the disclosure will become more apparent in view of the following detailed description when taken in conjunction with the accompanying drawings wherein like reference numerals identify similar or identical elements.

DETAILED DESCRIPTION

This disclosure relates to energy management. The operational life of a device (e.g., a sensor device) is determined by a variety of factors. Those factors typically include the amount of power capable of being supplied by a battery component of the device.

Thus, one way to increase the operational life of a device is to increase the size of its battery. However, a larger battery results in a larger device, which increases user burden. This is particularly true when the device is wearable.

To increase device operational life without increasing battery size, disclosed herein are techniques for minimizing battery power consumption prior to device deployment. More specifically, the techniques may be related to a mechanism for transitioning between a pre-deployment state and a deployed state. The mechanism may include a switch that is configured to transition between an open configuration and a closed configuration to control battery power consumption. In the pre-deployment state, the switch may be maintained in the closed configuration to minimize or prevent battery power consumption. In the deployed state, the switch may transition to an open configuration to facilitate battery power consumption.

Although the following description relates to various embodiments of a sensor assembly for monitoring glucose levels, it should be appreciated that the disclosed techniques are not limited to glucose sensor devices or even to sensor devices in general. Indeed, the techniques disclosed herein are equally applicable to any battery-powered device including, without limitation, a drug delivery device, a pacemaker, a smartwatch, or computing eyewear.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other non-transitory information storage media that may store instructions to perform operations and/or processes. As used herein, "exemplary"

does not necessarily mean "preferred" and may simply refer to an example unless the context clearly indicates otherwise.

Figure 1:
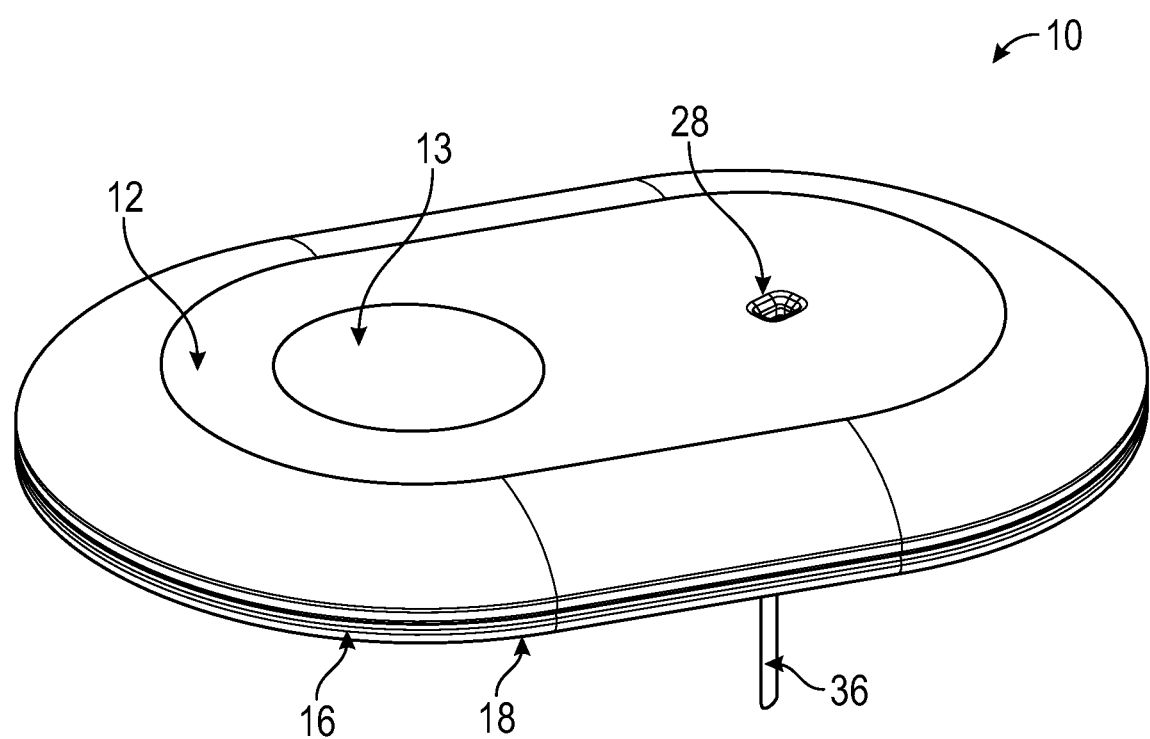
FIG. 1 is a perspective view of a sensor assembly, in accordance with aspects of the disclosure.
Figure 2:
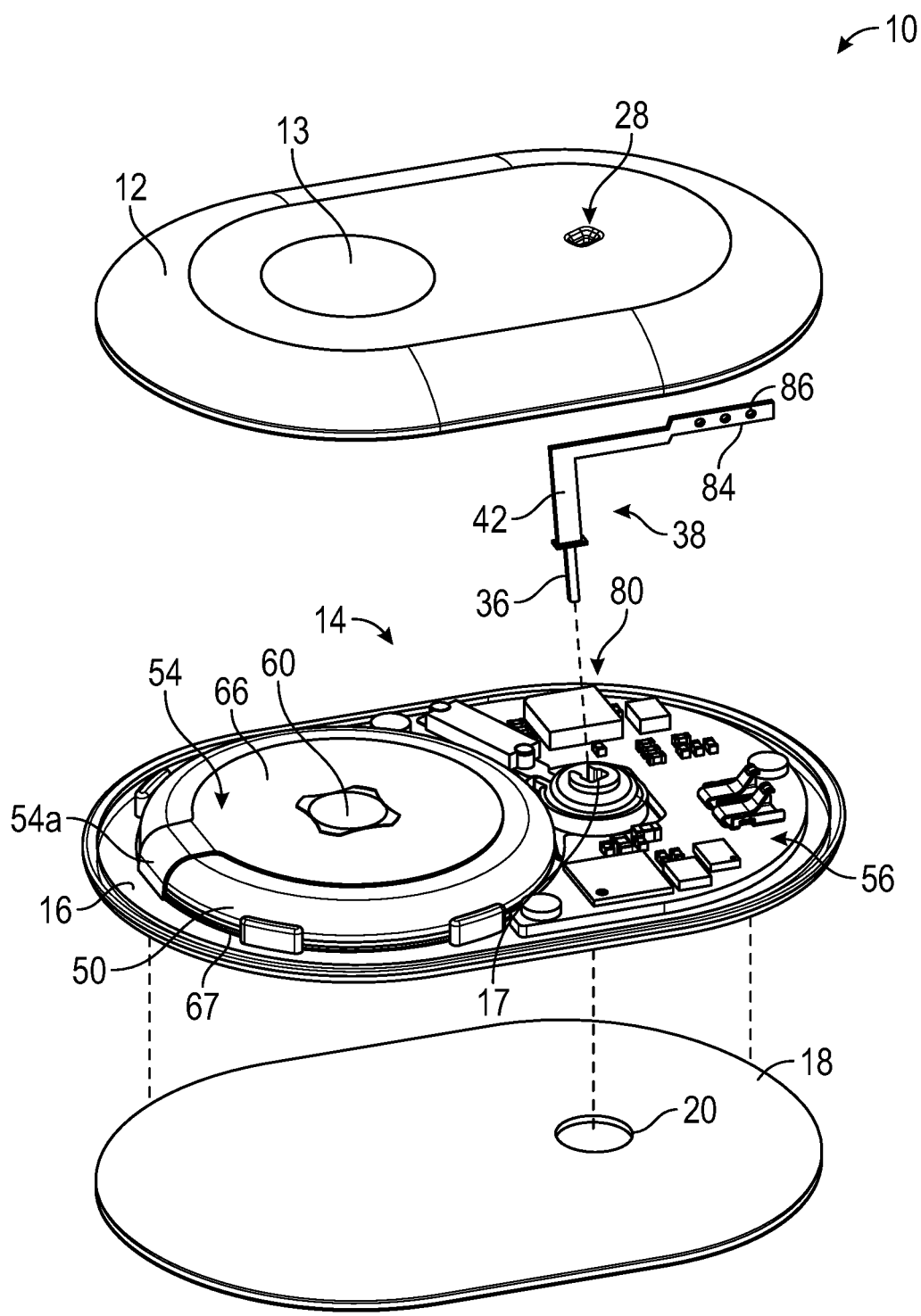
FIG. 2 is an exploded view of the sensor assembly of FIG. 1, in accordance with aspects of the disclosure.

With reference to FIGS. 1 and 2, a sensor assembly 10 is shown in accordance with embodiments of the disclosure and generally includes a top housing 12, an electrical subsystem 14, a lower housing 16, and an adhesive patch 18 coupled to the lower housing 16. In some embodiments, the top housing 12 and the lower housing 16 may be integrated into a single housing component. The top housing 12 is opposite the lower housing 16 and the adhesive patch 18. The top housing 12 forms a portion of an outermost surface of the sensor assembly 10. In the example of FIG. 1, the top housing 12 includes a depressible region 13. However, it should be appreciated that the depressible region 13 may be included in the lower housing 16 in some embodiments.

Although the depressible region 13 is depicted in FIG. 1 as being generally circular in shape, it should be appreciated that the depressible region 13 may be non-circular in some embodiments. For example, the depressible region 13 may be rectangular. In some embodiments, the top housing 12 (or the lower housing 16) may be a separate component from the depressible region 13. For example, the depressible region 13 may be a push button that frictionally engages an opening of the top housing 12. In some embodiments, the top housing 12 (or the lower housing 16) and the depressible region 13 may be composed of different materials. For example, the top housing 12 may be composed of a rigid material, and the depressible region 13 may be composed of a flexible material. In some embodiments, the top housing 12 (or the lower housing 16) and the depressible region 13 may be composed of the same material (e.g., a rigid material), but region 13 may be thinner than the top housing 12 (or the lower housing 16) so that region 13 can be flexible relative to the top housing 12 (or the lower housing 16). In some embodiments, the top housing 12 (or the lower housing 16) and the depressible region 13 may be composed of the same material (e.g., a rigid material), but region 13 may be at least partially surrounded by one or more grooves (e.g., a circular groove or a pair of linear grooves positioned at opposite sides of a rectangular region 13) so that region 13 can be flexible relative to the top housing 12 (or the lower housing 16).

In the example of FIG. 1, the depressible region 13 includes an outer surface that is substantially flush with an outer surface of the top housing 12 such that the depressible region 13 does not protrude outward relative to the outer surface of the top housing 12 or vice-versa. However, in some embodiments, the depressible region 13 may not be flush with the top housing 12 (or the lower housing 16). The depressible region 13 is configured to be depressed inward (e.g., toward the space enclosed by the top housing 12 and the lower housing 16) upon the application of a suitable force thereon. In some embodiments, the depressible region 13 is formed of a biocompatible polymer, including, but not limited to, a polyphenyl ether, thermoplastic polyurethane, silicone, etc. As discussed in further detail below with respect to FIGS. 9A and 9B, actuation of the depressible region 13 may serve to transition a switch within the sensor assembly 10 between a disabled state and an enabled state to control the supply of power from a battery 50 to the electrical subsystem 14. In some embodiments, when the switch is transitioned to the enabled state, the battery 50 may be caused to supply power to one or more components of the electrical subsystem 14. In such embodiments, when the switch is in the disabled state, consumption of power from the battery 50 may be minimized or prevented.

The top housing 12 includes a needle port 28 extending therethrough. As discussed in more detail below, the needle port 28 cooperates with a sensor introducer 110 (FIG. 6) to couple a sensor 38 to the body of a user. The needle port 28 enables a needle 256 of the sensor introducer 110 (FIG. 7) to be inserted through the sensor assembly 10 to insert a distal end portion 36 of the sensor 38 into subcutaneous tissue of the user.

With reference to FIG. 2, the sensor 38 includes the distal end portion 36, a proximal end portion 84 and a needle-accommodating portion 42 that extends from the distal end portion 36 toward the proximal end portion 84. In this example, the sensor 38 is substantially L-shaped, with the proximal end 84 extending outwardly from the needle-accommodating portion 42 at about a 90-degree angle. The proximal end 84 includes one or more sensor contacts 86. In some embodiments, the sensor 38 is an electrochemical sensor that includes the glucose oxidase enzyme, as is well understood by those familiar with glucose sensor technology. The glucose oxidase enzyme enables the sensor 38 to monitor glucose levels in a diabetic person by effecting a reaction involving glucose and oxygen. Again, although certain embodiments pertain to glucose sensors, the sensor assemblies described herein can be adapted for use with any one of the wide variety of sensors known in the art. Generally, the sensor 38 is positionable in subcutaneous tissue of the user by the needle 256 of the sensor introducer 110.

The lower housing 16 of the sensor assembly 10 is substantially planar and may be flexible. In some embodiments, the lower housing 16 is composed of a biocompatible polymer, including, but not limited to, polyethylene terephthalate. The lower housing 16 may be molded, three-dimensionally printed, cast, etc. The lower housing 16 cooperates with the top housing 12 to enclose the electrical subsystem 14. In some embodiments, the lower housing 16 is coupled to the top housing 12 by thermal welding, however, the lower housing 16 may be coupled to the top housing 12 through any suitable technique, including, but not limited to RF welding, laser welding, ultrasonic welding, epoxy, double sided adhesives, etc. The lower housing 16 includes a sensor bore 17 defined therethrough. The sensor bore 17 receives the distal end portion 36 of the sensor 38 therethrough. The adhesive patch 18 is coupled to the lower housing 16 and affixes the lower housing 16, and thus, the sensor assembly 10, to the skin of the user. The adhesive patch 18 may be composed of a flexible and breathable material with one or more adhesive layers, such as cloth, a bandage-like material, or the like. For example, suitable materials could include polyurethane, polyethylene, polyester, polypropylene, polytetrafluoroethylene (PTFE), or other polymers, to which one or more adhesive layers are applied. The adhesive patch 18 also defines a sensor bore 20 that extends through the adhesive patch 18 and enables the distal end portion 36 of the sensor 38 to pass through the adhesive patch 18 for subcutaneous placement into the body of the user.

The electrical subsystem 14 is disposed between the top housing 12 and the lower housing 16 and, in some embodiments, may be a printed circuit board assembly (PCBA) configured to be electrically coupled to the battery 50. Examples of a PCBA include, but are not limited to, a rigid-flex PCBA, a flex PCBA, a rigid PCBA, or the like. In the example shown in FIGS. 2 and 3, the electrical subsystem 14 is a rigid-flex PCBA including a rigid portion 56 and a flexible battery-contact portion 54 coupled to the rigid portion 56 and having a pair of electrically conductive battery contact pads 66 and 67 configured to make physical contact with the battery 50. The battery 50, in some embodiments, may be a 3.0V lithium battery. As detailed below, the battery 50 provides power to one or more components of the electrical subsystem 14 when the sensor assembly 10 is in the deployed state (e.g., deployed to a user and no longer coupled to the sensor introducer 110). In the example of FIG. 2, the battery 50 is a coin-cell battery. It should be noted that in some other embodiments the battery 50 may be a flexible thin film battery.

Figure 3:
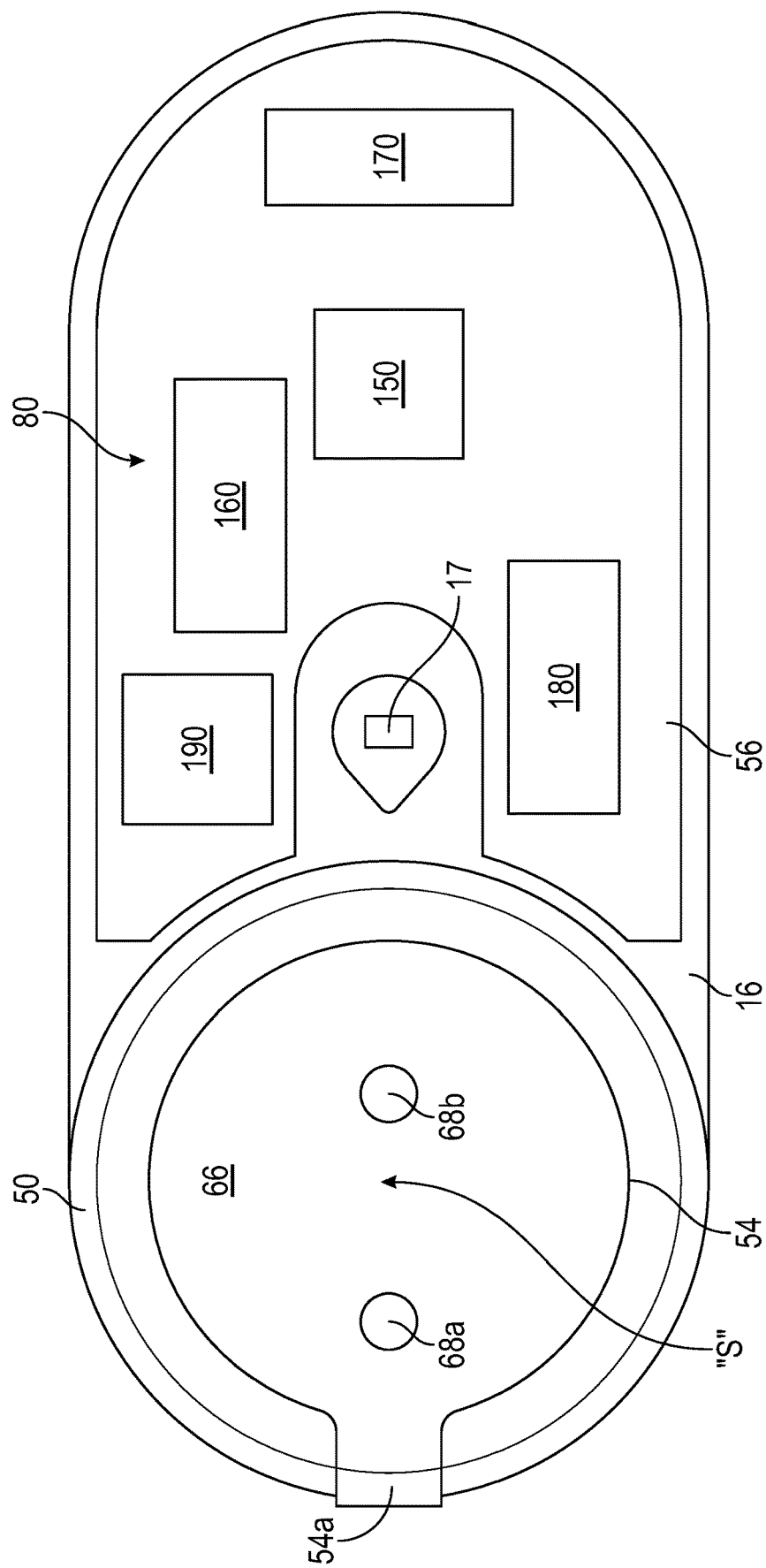
FIG. 3 is a top view of an electrical subsystem of the sensor assembly of FIG. 1, in accordance with aspects of the disclosure.
Figure 4:
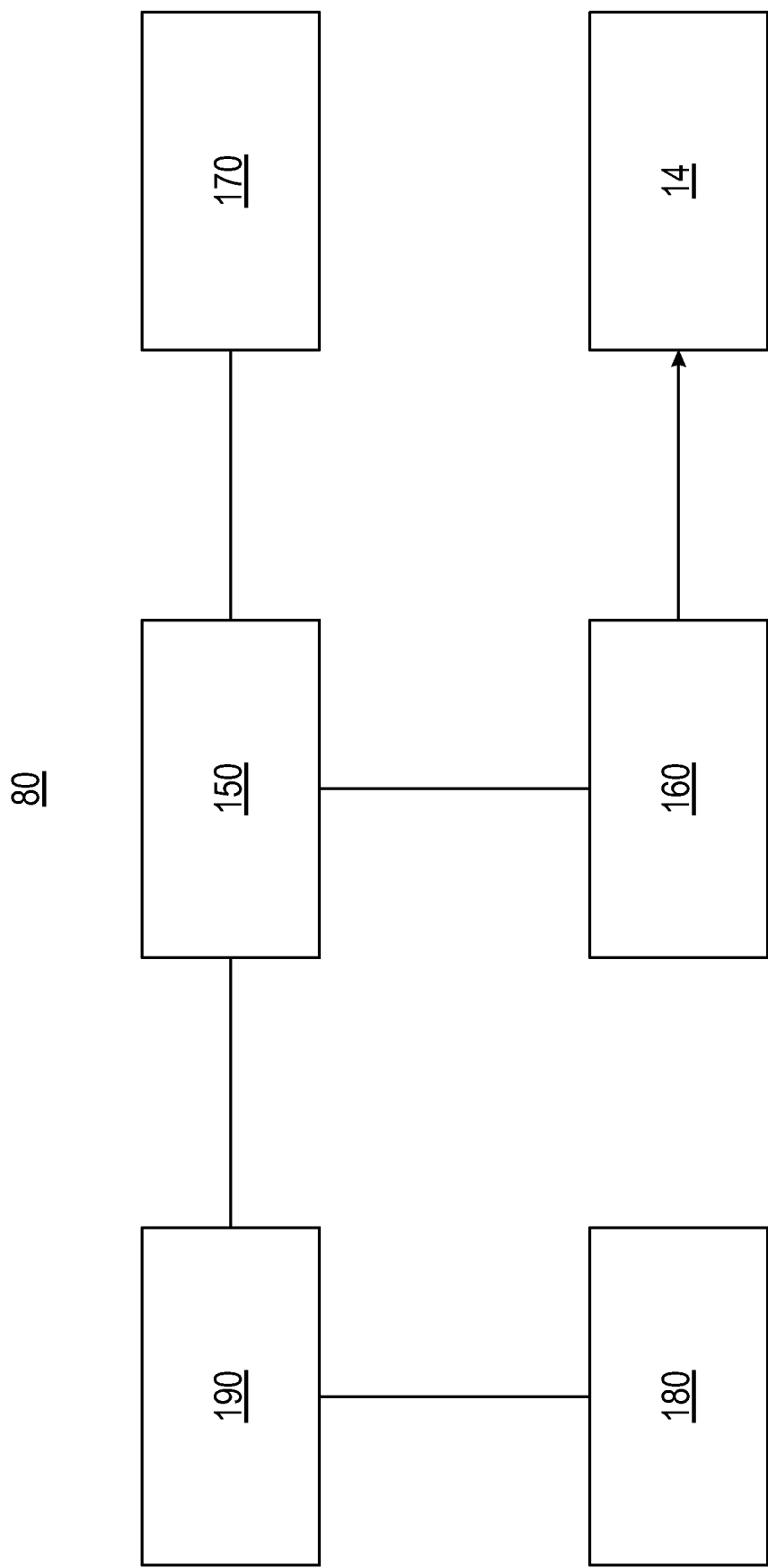
FIG. 4 is a schematic diagram of electrical components of the electrical subsystem of FIG. 3, in accordance with aspects of the disclosure.

With reference to FIG. 3, the battery-contact portion 54 and the rigid portion 56 of the exemplary electrical subsystem 14 are shown coupled to the lower housing 16. The battery-contact portion 54, in some embodiments, may be composed of a flexible material suitable to facilitate wrapping the battery-contact portion 54 around the battery 50. The rigid portion 56, in some embodiments, may be composed of a rigid material and secured to an inner surface of the lower housing 16. In some embodiments, the rigid portion 56 may be electrically and physically coupled to the battery-contact portion 54. The rigid portion 56 is electrically coupled to various electrical components 80 including, but not limited to, the sensor 37; a controller 150; a power control circuit 160; an antenna 170; a sensor interface 180; and an analog front end 190. The electrical components 80 are operably coupled to each other via the rigid portion 56 and are shown as a block diagram in FIG. 4. As detailed below, the power control circuit 160 serves to minimize or prevent delivery of power from the battery 50 to the various components of the electrical subsystem 14 when the sensor assembly 10 is in a pre-deployment state (e.g., coupled to the sensor introducer 110 and not yet deployed to a user) and serves to facilitate delivery of power from the battery 50 to one or more of the electrical components 80 of the electrical subsystem 14 when the sensor assembly 10 in the deployed state.

The battery-contact portion 54 electrically couples the battery 50 to the rigid portion 56 to enable delivery of power from the battery 50 to the electrical components 80. With reference to FIG. 3, a top side of the battery-contact portion 54 and the rigid portion 56 are shown. As mentioned above, in some embodiments, the depressible region 13 may be disposed on the lower housing 16. In such embodiments, FIG. 3 would correspond to the bottom side of the battery-contact portion 54 and/or the bottom side of the rigid portion 56.

The battery contact pad 66 is separated from the battery contact pad 67 by a thin portion 54a of the battery-contact portion 54, which enables the battery contact pad 66 to be folded over the battery 50 so that the battery contact pad 66 is vertically aligned with the battery contact pad 67. One of the battery contact pads 66, 67 couples with a positive terminal of the battery 50, and the other of the battery contact pads 66, 67 couples with a negative terminal of the battery 50.

The antenna 170 enables wireless communication between the sensor assembly 10 and another device, including, but not limited to, an infusion pump or a wireless handheld computing device (tablet, smart phone, etc.). In some embodiments, the antenna 170 may be a trace antenna formed on or coupled to the rigid portion 56. In some other embodiments, the antenna 170 may be a chip antenna, wire antenna, or a stamped metal antenna. In some embodiments, the antenna 170 may be a Bluetooth low energy (BLE) trace antenna. It should be noted, however, that the antenna 170 may be any of a variety of antennas including, but not limited to, a near field communication (NFC) antenna, RF radio antenna, a far field communication antenna, a wireless communication system configured to communicate via a wireless local area network (WLAN) using IEEE 802.11 standards or by using cellular data communication, a Bluetooth antenna, etc. In certain embodiments, the antenna 170 may include more than one communication device, such as a near field communication (NFC) antenna and a Bluetooth low energy (BLE) trace antenna.

The controller 150 may include one or more processors and one or more processor-readable storage media (e.g., memory). Each of the one or more processors can be any custom made or commercially available processor, a central processing unit (CPU), a graphics processing unit (GPU), an auxiliary processor among several processors associated with the controller 150, a semiconductor based microprocessor (in the form of a microchip or chip set), a macroprocessor, any combination thereof, or generally any device for executing instructions. The processor may also include digital signal processors (DSPs), general purpose microprocessors, application specific integrated circuits (ASICs), field programmable logic arrays (FPGAs), or other equivalent integrated or discrete logic circuitry. The one or more processor-readable storage media may include volatile and/or nonvolatile storage devices, such as read-only memory (ROM), random-access memory (RAM), and keep-alive memory (KAM), for example. KAM is a persistent or nonvolatile memory that may be used to store various operating variables while the processor is powered down. The one or more processor-readable storage media may be implemented using any of a number of known memory devices such as PROMs (programmable read-only memory); EPROMs (electrically PROM); EEPROMs (electrically erasable PROM); flash memory; or any other electric, magnetic, and/or optical memory devices. The one or more processor-readable storage media are capable of storing data, some of which may correspond to executable instructions, used by the controller 150 in controlling components associated with the sensor assembly 10. For example, the one or more processor-readable storage media may store data used by the controller 150 to receive sensor signals from the sensor 38 as input and transmits these sensor signals, via the antenna 170, to a remote device, including, but not limited to, an infusion pump or a handheld device (tablet, smart phone, etc.). The electrical components 80 may also include an additional communication system, including, but not limited to, a wireless communication system configured to communicate via a wireless local area network (WLAN) using IEEE 802.11 standards or by using cellular data communication, a Bluetooth antenna, etc.

The lower housing 16 includes a sensor bore 17 defined therethrough. The sensor bore 17 enables the needle 256 of the sensor introducer 110 (FIG. 7) to pass through the lower housing 16 and into the needle-accommodating portion 42 (FIG. 2) of the sensor 38. The sensor contacts 86 of the sensor 38 electrically couple the sensor 38 to the sensor interface 180 on the rigid portion 56. The sensor interface 180 communicates analog sensor signals received from the sensor 38 to the analog front end 190, which serves to convert the analog sensor signals to digital signals for communication to the controller 150. As discussed below with respect to the embodiment of FIGS. 9A and 9B, the depressible region 13 (FIG. 2) may serve to either enable or disable a switch "S" defined between a first contact pad 68a and a second contact pad 68b of the battery contact pad 66. In some embodiments, transition of the sensor assembly 10 to the deployed state enables (e.g., opens or closes) the switch "S", thereby triggering the power control circuit 160 to facilitate delivery of power from battery 50 to one or more components of the electrical subsystem 14. Likewise, while the sensor assembly 10 is in the pre-deployment state and/or prior to transition of the sensor assembly 10 to the deployed state, the switch "S" is disabled and the power control circuit 160 minimizes or prevents delivery of power from the battery 50 to the electrical subsystem 14.

Figure 5A:
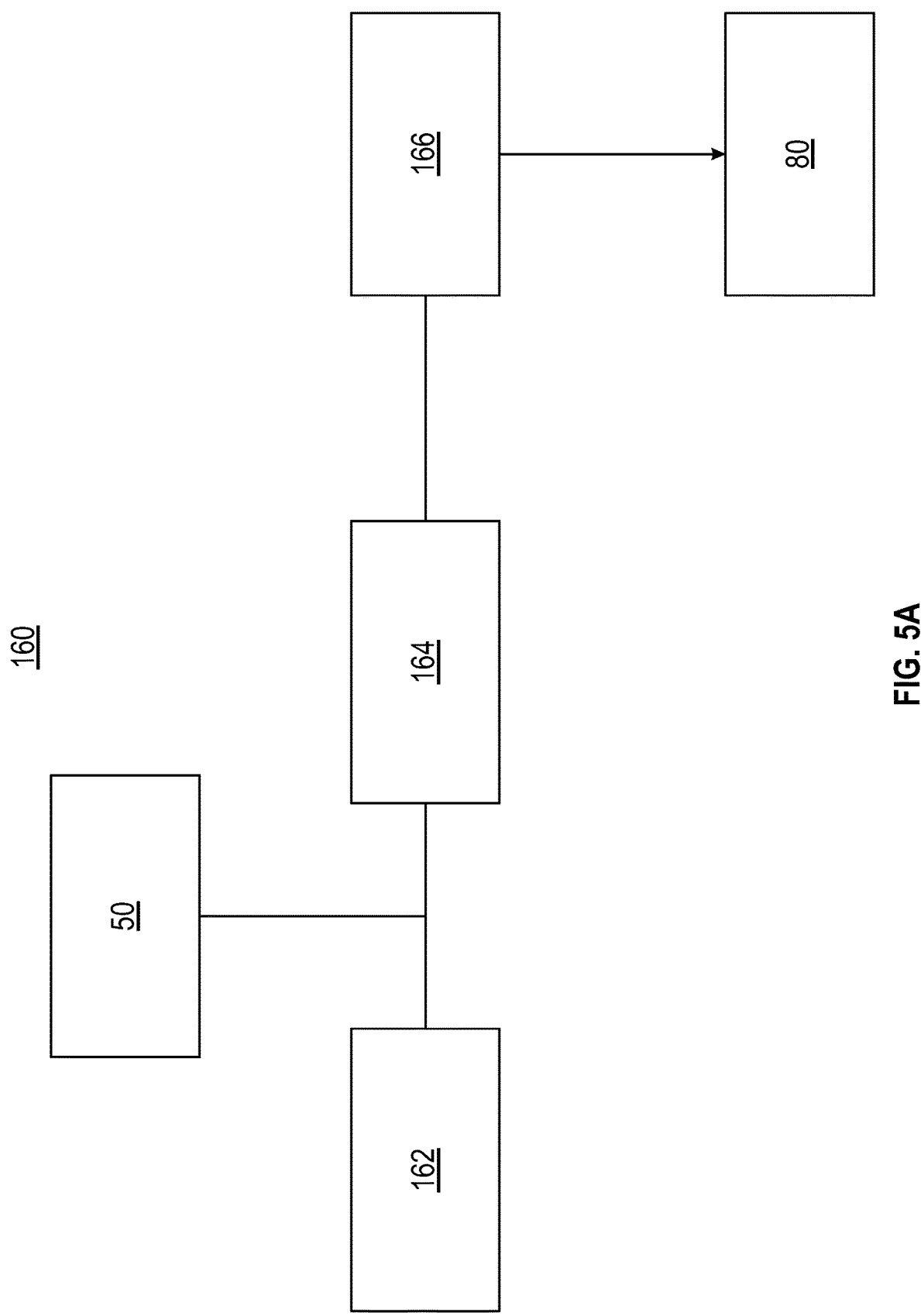
FIG. 5A is a schematic diagram of a power control circuit of the electrical components of FIG. 4, in accordance with aspects of the disclosure.

Referring now to FIG. 5A, a block diagram of an exemplary power control circuit 160 and exemplary components thereof are shown. The power control circuit 160 is electrically coupled to the battery 50 and serves to minimize or prevent battery power consumption by the electrical subsystem 14 of the sensor assembly 10 prior to deployment of the sensor assembly 10 to a user (e.g., while the sensor assembly 10 is in the pre-deployment state). The power control circuit 160 also serves to facilitate delivery of power from the battery 50 to the electrical subsystem 14 indefinitely upon deployment of the sensor assembly 10 to a user (e.g., when the sensor assembly 10 transitions to the deployed state). With this purpose in mind, the power control circuit 160 generally includes an analog controller switch 164 having an input coupled to the battery 50 and an output coupled to an input of a power converter 166 (e.g., a buck converter). The controller switch 164 is operably coupled with a power latch 162, which may be built in the controller switch 164 or may be disposed separate from and coupled to the controller switch 164, as shown in the example of FIG. 5A. In some embodiments, the controller switch 164 may consume a maximum of about 20 nA of standby current (e.g., while the controller switch 164 is in a standby state) to ensure minimal drain on the battery 50 while the sensor assembly 10 is in the pre-deployment state and/or the switch "S" is disabled. In some embodiments, the power converter 166 may consume a maximum of about 5 nA of shutdown current (e.g., while the power converter 166 is in a shutdown state) to ensure minimal drain on the battery 50 while the sensor assembly 10 is in the pre-deployment state and/or the switch "S" is disabled. Thus, in some embodiments, the power control circuit 160 may consume a maximum of about 25 nA of current while the sensor assembly 10 is in the pre-deployment state and/or the switch "S" is disabled. In some aspects, the power converter 166 may consume a maximum of about 5 nA of standby current (e.g., while the power converter 166 is in a standby state) to ensure minimal drain on the battery 50 while the sensor assembly 10 is in the pre-deployment state and/or the switch "S" is disabled.

Upon enabling of the switch "S", the controller switch 164 accepts an input signal from the switch "S" and, in response, provides an output to the power converter 166. It will be appreciated that the power latch 162 serves to lock the output of the controller switch 164 in response to application of a momentarily input trigger signal (e.g., a momentary input signal generated by enablement of the switch "S"), and to retain that state even after the input trigger signal is removed. In this way, a momentary enabling (e.g., closing or opening) of the switch "S" upon deployment of the sensor assembly 10 to the user triggers the power latch 162 to maintain the output of the controller switch 164 to the power converter 166 such that the latched output of the power control circuit 160 serves to power one or more components of the electrical subsystem 14 indefinitely, even after the input signal from the switch "S" is removed. This state may remain indefinitely until the controller switch 164 is returned to a standby state (e.g., via application of an external signal to the controller switch 164).

In some embodiments, the controller switch 164 may include a built-in switch debouncer to debounce the input from the switch "S" and/or mitigate the effects of the switch "S" bouncing. The controller switch 164, in some embodiments, may provide output only after the debounce interval of the switch debouncer so that the controller switch 164 avoids outputting a non-debounced signal (e.g., chatter, ripple signal, etc.) caused by bouncing at the switch "S".

In some embodiments, when the switch "S" is disabled (e.g., when the sensor assembly 10 is in a pre-deployment state), electrical connection between the battery 50 and the power control circuit 160 may be entirely interrupted (e.g., an open circuit) such that there is no consumption of power from the battery 50 by the power control circuit 160 or other components of the electrical subsystem 14. In other embodiments, when the switch "S" is disabled, there may be an electrical connection (e.g., a closed circuit) between the battery 50 and the power control circuit 160. In such other embodiments, the power control circuit 160 may consume only standby current and/or shutdown current. For example, when the switch "S" is disabled and there is no load (e.g., the electrical subsystem 14) on the power control circuit 160, one or both of the controller switch 164 and the power converter 166 may be enabled and consuming standby current or one or both of the controller switch 164 and the power converter 166 may be disabled and consuming only shutdown current. In one specific example, when the switch "S" is disabled the controller switch 164 is enabled and consuming a standby current of about 20 nA and the power converter 166 is disabled and consuming a shutdown current of about 5 nA. In this specific example, the power control circuit 160 is consuming a relatively small amount of current (e.g., about 25 nA) to ensure minimal drain on the battery 50 when the sensor assembly 10 is in a pre-deployment state and prior to enabling of the switch "S", thereby maximizing the life of the battery 50 and, thus, the operational life of the sensor device 10.

In some embodiments, when the switch "S" is enabled (e.g., when the sensor assembly 10 is in the deployed state), electrical connection between the battery 50 and the power control circuit 160 serves to facilitate delivery of power from the battery 50 to one or more components of the electrical subsystem 14. More specifically, upon enabling of the switch "S", a signal received at an input of the controller switch 164 causes the power latch 162 to latch the output of the controller switch 164 and provided to an input of the power converter 166. The power converter 166 steps down the voltage of the latched input signal received from the controller switch 164 to relatively lower voltages in accordance with the voltage needs of the various components of the electrical subsystem 14. The stepped-down output of the power converter 166 is provided to one or more components of the electrical subsystem 14 indefinitely until the power is reset or an external signal is applied to the controller switch 164 to return the controller switch 164 to a standby state.

Figure 5B:
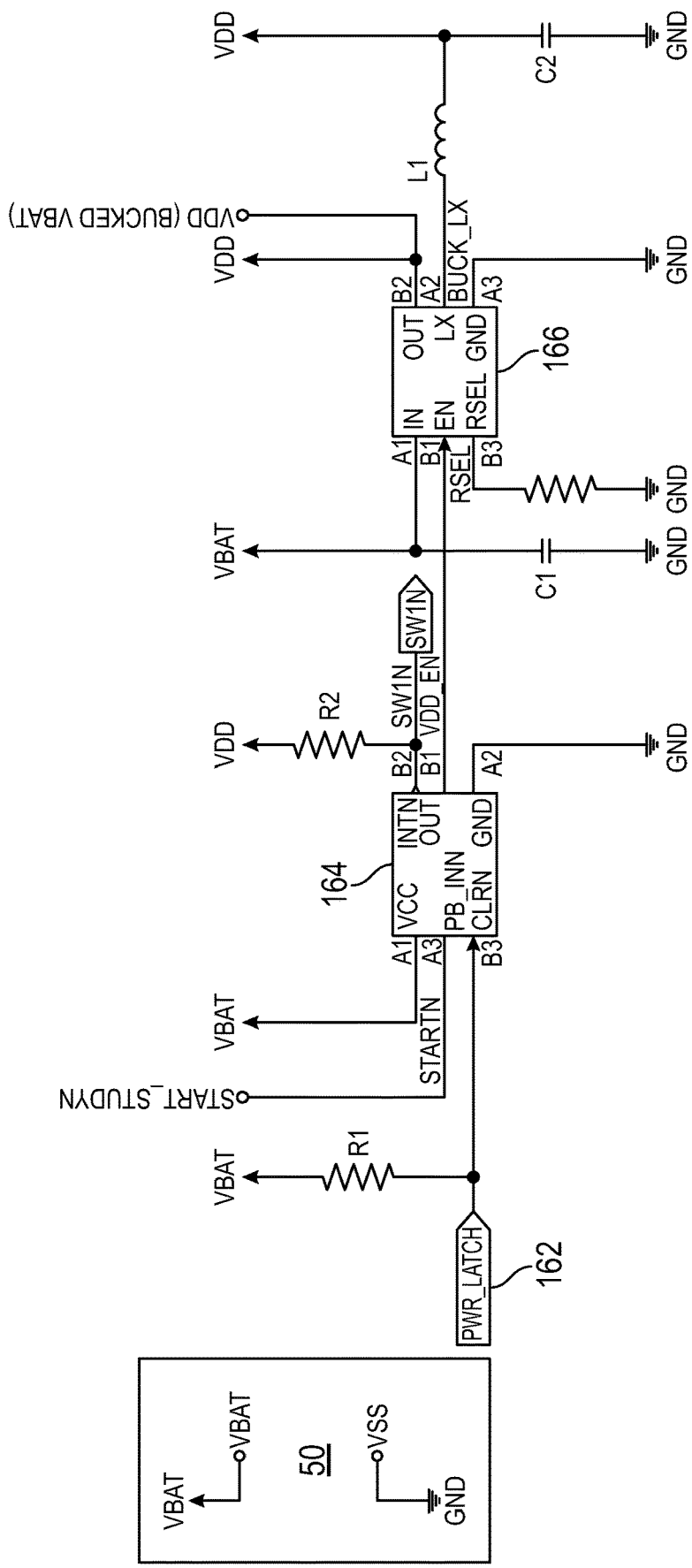
FIG. 5B is a circuit diagram of a power control circuit of the electrical components of FIG. 4, in accordance with aspects of the disclosure.

Referring now to FIG. 5B, a circuit diagram of a non-limiting exemplary embodiment of the power control circuit 160 of FIG. 5A and non-limiting exemplary components thereof are shown. It should be understood that the exemplary embodiment of the power control circuit 160 shown in FIG. 5B operates substantially as described above with respect to FIG. 5A and will only be described to the extent necessary to specify the functions of the exemplary components. In the exemplary embodiment of FIG. 5B, the power converter 166 may be a buck (step-down) converter that operates from 1.8V to 5.5V input voltage. The power converter 166 may consume a maximum of about 330 nA of quiescent current when not driving an output and, when in shutdown mode, may consume a maximum of about 5 nA of shutdown current. The controller switch 164 may be a pushbutton on/off controller that operates from a supply range of +1.3V to +5.5V and includes a built in switch debounce circuit. The controller switch 164 may consume a maximum of about 20 nA of standby current (e.g., while the controller switch is in a standby state) and be configured to supply a latched output of about 20 mA of load current to one or more components of the electrical subsystem 14.

$V_{DD}$ is the switched, buck-converted system voltage that is delivered to one or more components of the electrical subsystem 14. $V_{BAT}$ is the power from the battery 50 that is always present. The power control circuit 160 of FIG. 5B includes chip resistors R1, R2, R3, an inductor L1 coupled to the inductor drive pin LX of the power converter 166 for storing energy, and input and output capacitors C1 and C2, respectively, coupled to the power converter 166. In some aspects of the exemplary embodiment, chip resistors R1 and R2 may each have a resistance of 4.7 kOhms±5% and resistor R3 may be coupled to the $R_{SEL}$ pin of the power converter 166 and serve to program the output voltage of the power converter 166 upon startup. In some aspects of the exemplary embodiment, resistor R3 may have a resistance of 768 KOhms±1%. In some aspects of the exemplary embodiment, the inductor L1 may have an inductance of 4.7 µH and capacitors C1 and C2 may have a capacitance of 18 µF and 22 µF, respectively.

The START_STUDYn line is an active low control signal coupled to the pushbutton input PB_INn of the controller switch 164. For initial power on (e.g., upon enablement of the switch "S"), the START_STUDYn line is pulled low and the output of the controller switch 164 is latched by the power latch 162 and provided as output by the OUT pin of the controller switch 164 to the enable EN pin of the power converter 166. The OUT pin of the controller switch 164 may be a push-pull latched output and connected to the power supply input $V_{CC}$ of the controller switch 164 when high. In some embodiments, the latched output of the controller switch 164 may only be cleared by asserting the asynchronous CLRn input of the controller switch 164, which causes the controller switch 164 to force the latched output to an off state (e.g., disable delivery of power from the battery 50 to the electrical subsystem 14). Once the switch "S" is enabled and the battery 50 is providing power to the controller switch 164, the START_STUDYn line may be used as a standard push button. The INTn line may be an active-low interrupt/reset output that generates a one-shot output pulse. The INTn line asserts for the interrupt timeout period when PB_INn is held low for a period greater than the debounce time. The INTn line is asserted via SW1n and can be detected by the controller 150.

Figure 6:
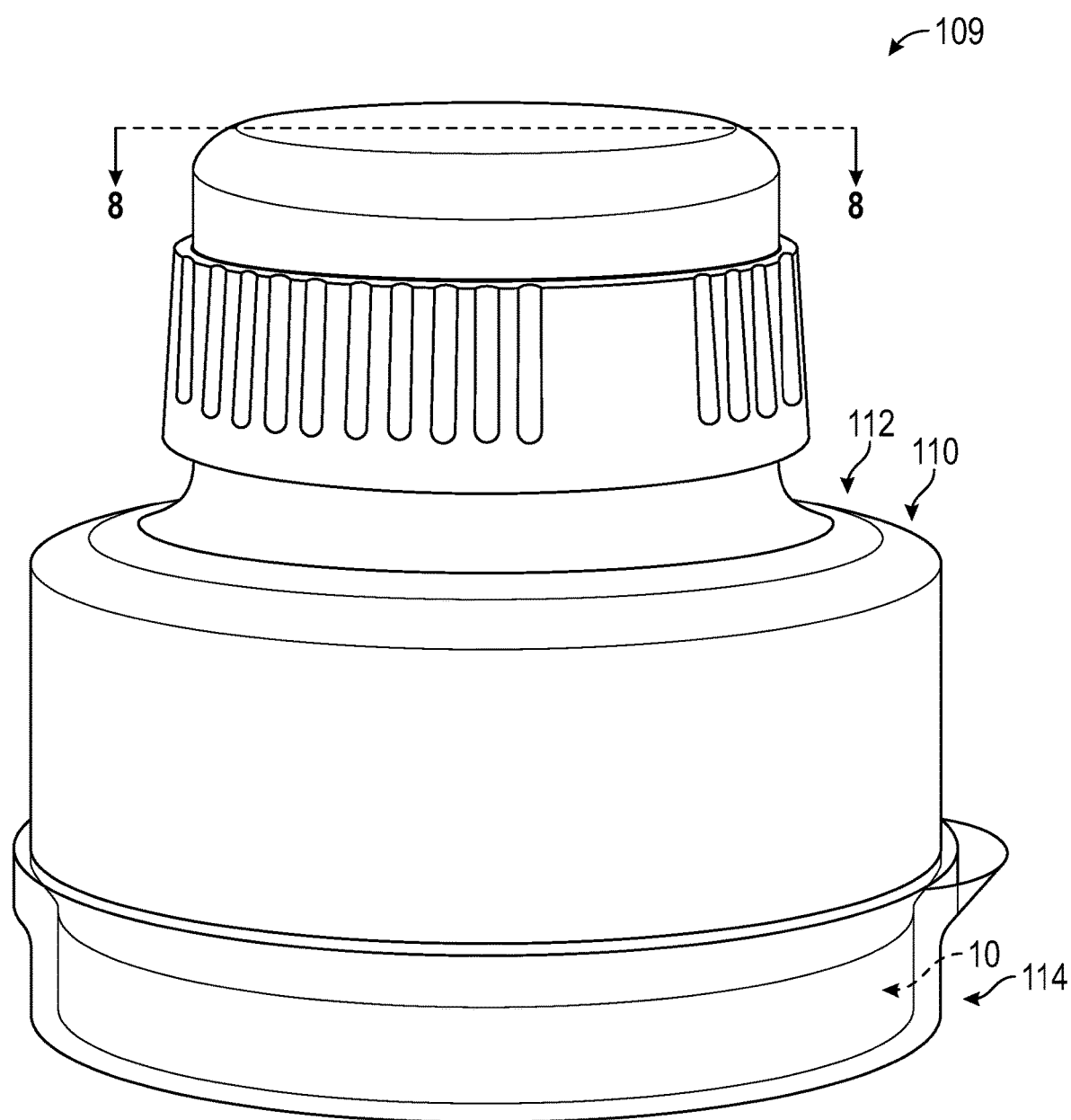
FIG. 6 is a perspective view of a sensor introducer for use with the sensor assembly of FIG. 1, in accordance with aspects of the disclosure.

Referring now to FIG. 6, the sensor introducer 110 may serve to deploy the sensor assembly 10 to a user (not shown). The sensor introducer 110 generally includes an introducer body 112 and a cover 114. As the sensor assembly 10 may be received wholly within the sensor introducer 110, the sensor introducer 110 may also be used to package and ship the sensor assembly 10. Thus, the sensor assembly 10 in combination with the sensor introducer 110 may be considered a sensor system 109.

Figure 7:
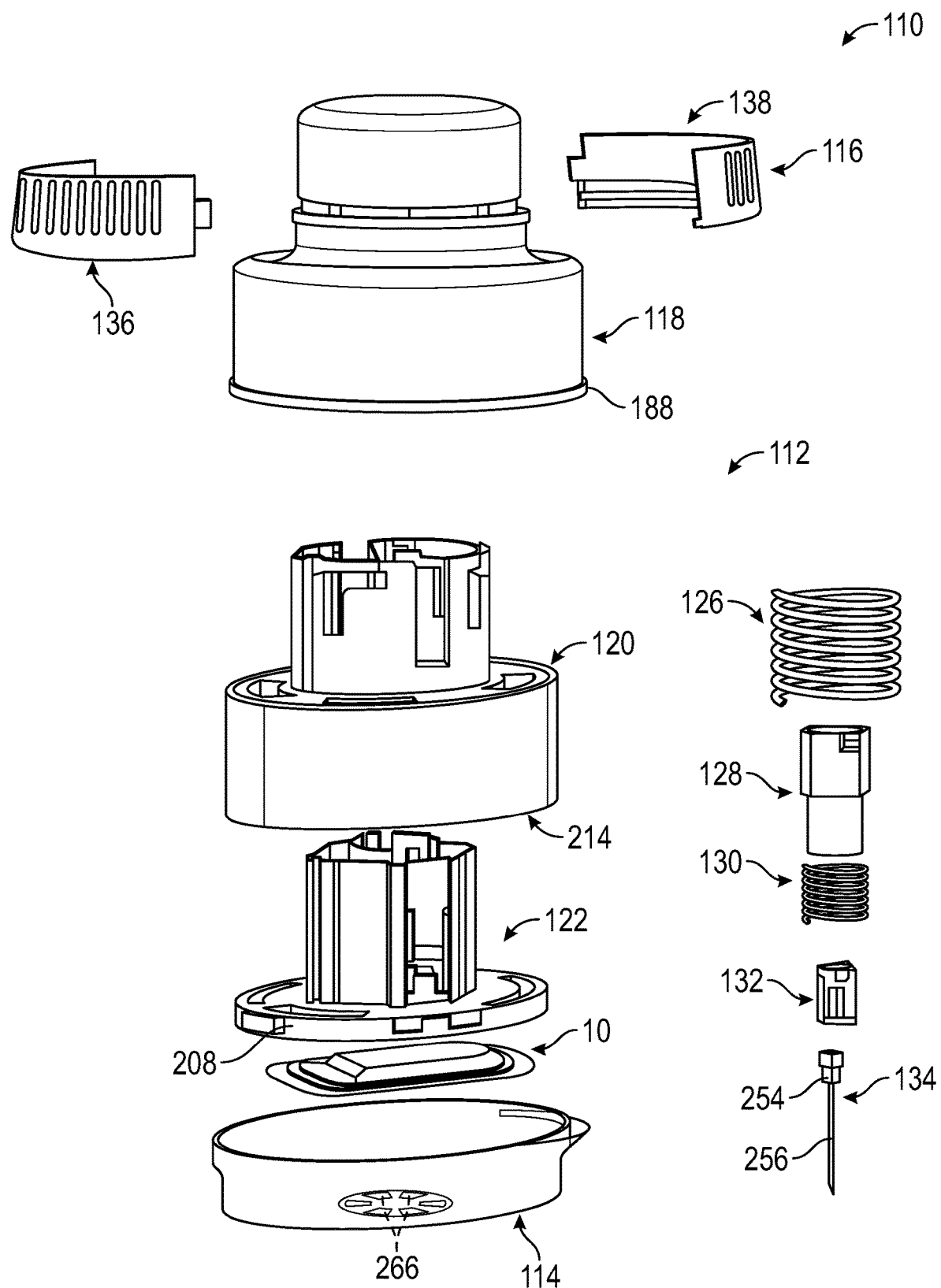
FIG. 7 is an exploded view of the sensor introducer of FIG. 6, in accordance with aspects of the disclosure.

With reference to FIG. 7, in some embodiments, the introducer body 112 includes a collar assembly 116, an outer housing 118, an inner housing 120, a cradle 122, a deployment spring 126, a needle shuttle 128, a retraction spring 130, a needle cradle 132, and a needle assembly 134. The sensor introducer 110 is transitionable from a first, retracted state to a second, deployed state. In the first state, the sensor assembly 10 may be coupled to the sensor introducer 110 but not deployed to a user. In the second state, the sensor assembly 10 may be deployed to a user and no longer coupled to the sensor introducer 110.

The collar assembly 116 includes a first collar ring 136 coupled to a second collar ring 138, both of which are coupled to the outer housing 118. The collar assembly 116 is rotatable to unlock the inner housing 120 from the outer housing 118. For example, the collar assembly 116 may rotate clockwise to unlock or release the inner housing 120. The outer housing 118 includes an opening 188, which enables the inner housing 120 to be received within the outer housing 118 such that the outer housing 118 surrounds the inner housing 120.

Figure 8:
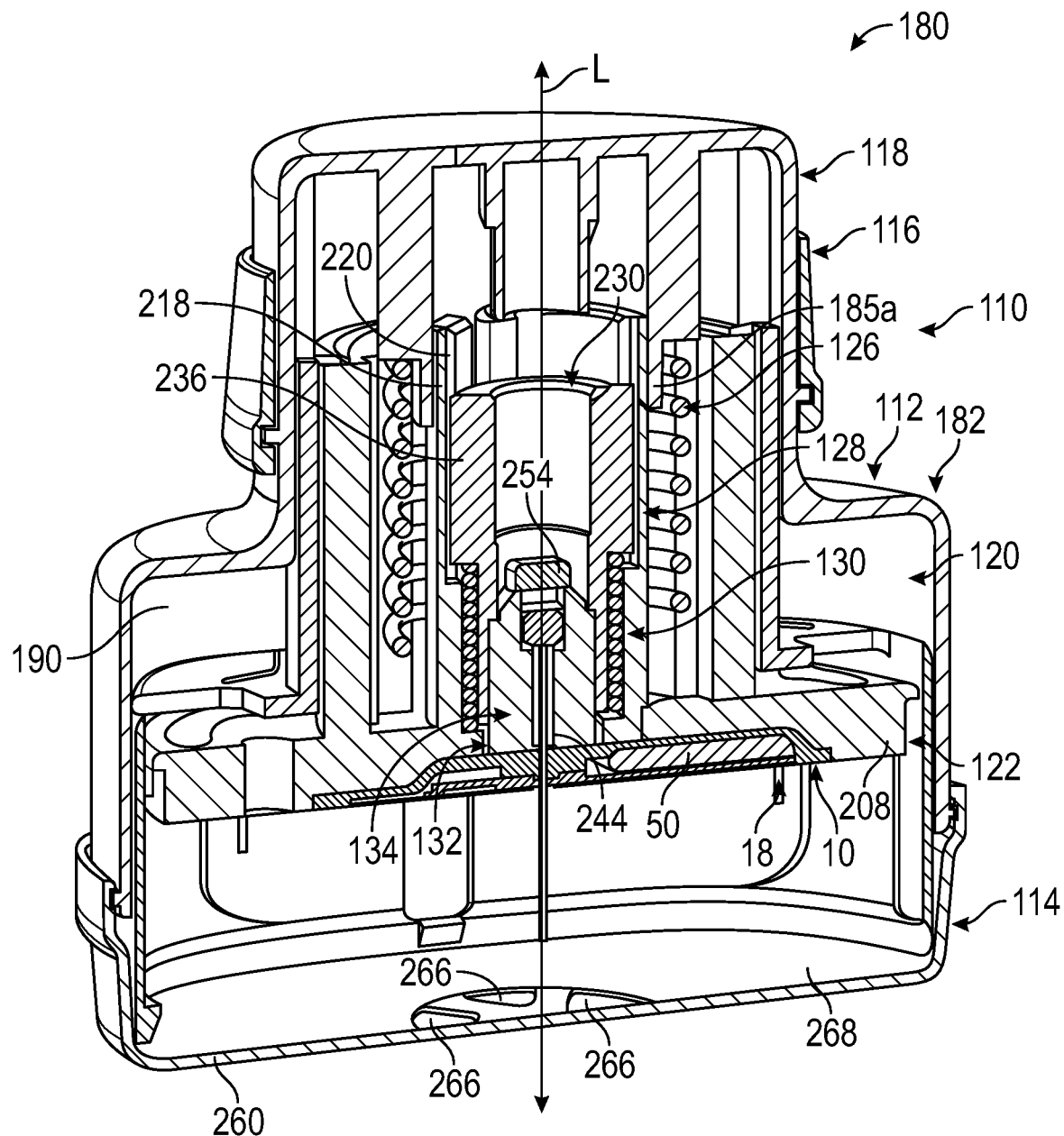
FIG. 8 is a cross-section of the sensor introducer of FIG. 6 in a first, retracted state, taken along line 8-8 of FIG. 6, in accordance with aspects of the disclosure.

With reference to FIGS. 7 and 8, the needle shuttle receptacle 214 receives the needle shuttle 128 to guide movement of the needle shuttle 128 relative to the cradle 122. The needle shuttle receptacle 214 may also include a stop feature (not shown) that contacts a portion of the needle shuttle 128 in the first, retracted state to prevent movement of the needle shuttle 128 beyond the stop feature.

The deployment spring 126 is a helical coil spring, which is composed of a suitable biocompatible material, such as a spring steel that is wound to form the deployment spring 126. In the example of FIG. 7, the deployment spring 126 is a compression spring, which is received between the outer housing 118 and the cradle flange 208. In the first, retracted state, the deployment spring 126 is positioned between the outer housing 118 and the cradle 122, and as the sensor introducer 110 transitions from the first, retracted state to the second, deployed state, the deployment spring 126 exerts a spring force along the longitudinal axis L to move the cradle 122 toward a bottom end of the inner housing 120 to deploy the sensor assembly 10 to the user.

The needle shuttle 128 guides the needle assembly 134 into the subcutaneous tissue of the user. The needle shuttle 128 is received within the needle shuttle receptacle 214 and is substantially cylindrical. The needle shuttle 128 defines a bore 230 that receives the needle cradle 132 and the needle assembly 134.

With reference to FIG. 8, the retraction spring 130 is a helical coil spring, which is composed of a suitable biocompatible material, such as a spring steel that is wound to form the retraction spring 130. In the example of FIG. 8, the retraction spring 130 is a compression spring, which is received between the needle guides 236 of the needle shuttle 128 and an upper surface of the cradle flange 208. In the first, retracted state, the retraction spring 130 is compressed between the needle shuttle 128 and the cradle 122.

The needle cradle 132 is cylindrical, is composed of a suitable polymer-based material, and may be cast, molded, printed, etc. The needle cradle 132 includes a bore 244 that receives the needle assembly 134 therethrough. The bore 244 is counterbored to receive a needle hub 254 of the needle assembly 134. The needle hub 254 may be coupled to the needle cradle 132 via adhesives, ultrasonic welding, press-fit, etc. With reference to FIG. 7, the needle cradle 132 engages the needle shuttle 128 to couple the needle cradle 132 to the needle shuttle 128 in such a manner that prevents linear and rotational movement of the needle cradle 132 relative to the needle shuttle 128. The needle assembly 134 includes the needle hub 254 and a needle 256 for piercing skin of the user to introduce the distal end portion 36 of the sensor 38 into the subcutaneous tissue of the user. The needle hub 254 couples the needle 256 to the needle cradle 132.

With reference to FIG. 8, the cover 114 is removably coupled to the outer housing 118 and surrounds a bottom end of the inner housing 120. The cover 114 may be composed of a suitable polymer-based material (including, but not limited to, silicon) and may be cast, molded, printed, etc. In the example of FIG. 8, the cover 114 includes a substantially planar base 260 having a plurality of openings 266 for venting. The base 260 defines a chamber 268 that receives a portion of the inner housing 120 such that the cover 114 surrounds a bottom end of the inner housing 120 to enclose the opening 188 of the outer housing 118. With the cover 114 removably coupled to the outer housing 118 and with the sensor assembly 10 removably coupled to the cradle 122, the sensor introducer 110 may be used as a shipping package for the sensor assembly 10. Thus, the sensor introducer 110 reduces the need for additional or separate packaging in order to ship and transport the sensor assembly 10.

Figure 9A:
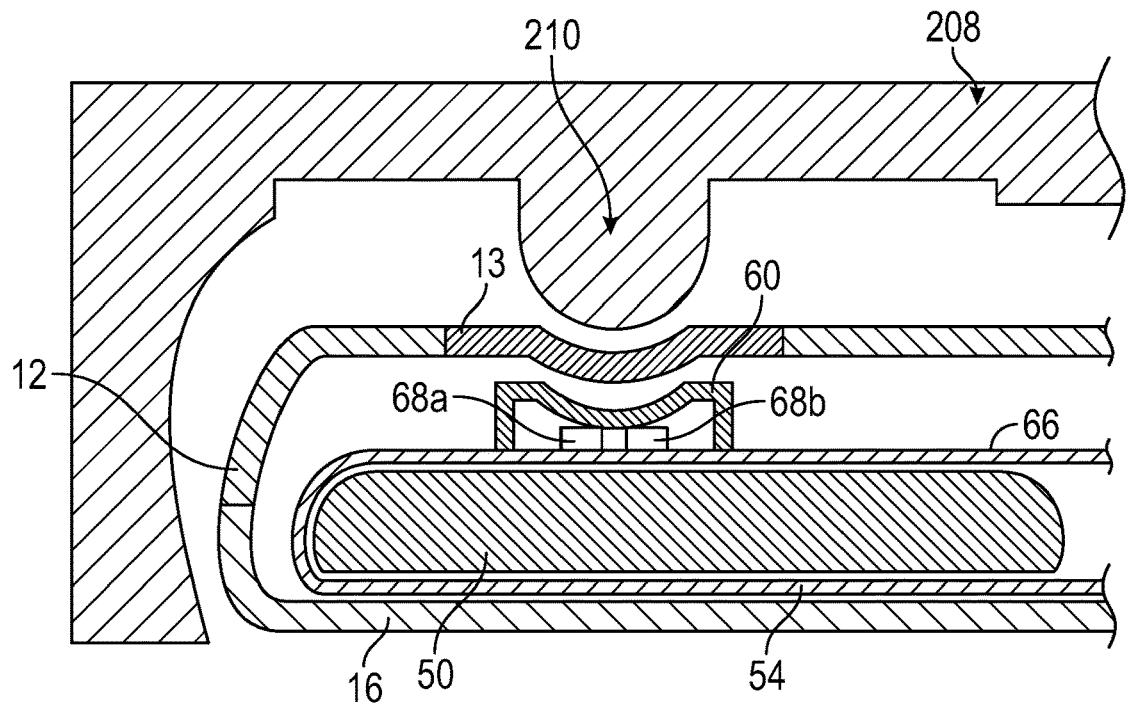
FIG. 9A is a cross-section of a portion of the sensor introducer of FIG. 6 and a portion of the sensor assembly of FIG. 1, with the sensor assembly removably coupled to the sensor introducer, the sensor introducer in a first, retracted state, in accordance with aspects of the disclosure.
Figure 9B:
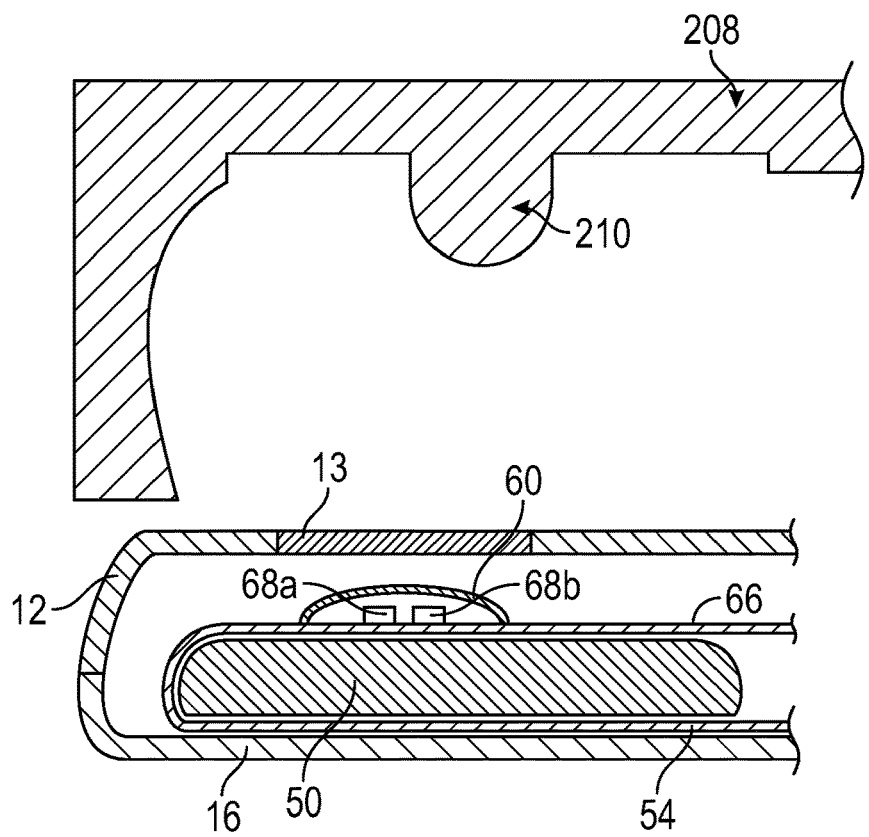
FIG. 9B is a cross-section of a portion of the sensor introducer of FIG. 6 and a portion of the sensor assembly of FIG. 1, with the sensor assembly uncoupled from the sensor introducer, the sensor introducer in a second, deployed state, in accordance with aspects of the disclosure.

With reference to FIGS. 9A and 9B, an embodiment of the sensor assembly 10 is shown that is configured such that battery power consumption is prevented or minimized prior to deployment of the sensor assembly 10 to a user (e.g., while the sensor assembly is in the pre-deployment state) and delivery of power from the battery 50 to one or more of components of the electrical subsystem 14 is facilitated and maintained by the power control circuit 160 when the sensor assembly 10 transitions to the deployed state. Thus, battery power consumption is prevented or minimized when the sensor assembly 10 is not used for monitoring glucose levels (e.g., during transportation and storage of the sensor assembly 10).

With reference to FIG. 9A, the sensor assembly 10 is shown removably coupled to the sensor introducer 110 in the retracted state of the sensor introducer 110 (e.g., prior to deployment of the sensor assembly 10 using the sensor introducer 110) according to some embodiments of the present disclosure. The flange portion 208 of the cradle 122 includes a protrusion 210 configured to vertically align with the depressible region 13 of the sensor assembly 10. When the sensor assembly 10 is removably coupled to the sensor introducer 110, the protrusion 210 depresses the region 13 relative to the top housing 12 of the sensor assembly 10. A momentary switch contact 60 (e.g., snap dome) is disposed between the battery contact pad 66 and the top housing 12 in general vertical alignment with the depressible region 13. When the sensor assembly 10 is removably coupled to the sensor introducer 110 (e.g., when the sensor assembly 10 is in a pre-deployment state), as shown in FIG. 9A, the region 13 and the switch contact 60 are depressed. Depression of the switch contact 60 serves to move the switch contact 60 into contact with the first and second contact pads 68a, 68b such that electrical continuity is established therebetween. In this state, the switch "S" is disabled such that the switch "S" does not trigger delivery of power from the battery 50 to the power control circuit 160. As detailed below, interruption of electrical continuity between the first and second contact pads 68a, 68b, as shown in FIG. 9B, may enable the switch "S" and serve as a momentarily input trigger signal to trigger delivery of power from the battery 50 to the power control circuit 160. In some embodiments, the switch contact 60 may be any one of a snap dome, a tactile dome, a metal dome, or the like, types of which include but are not limited to four-legged, three-legged, round, triangle, and oblong. In some embodiments, the switch contact 60 may be made from a suitable conductive material (e.g., stainless steel). In some embodiments, the switch contact 60 may be coupled to the depressible region 13, coupled to the battery contact pad 66, or coupled to both.

Following deployment of the sensor assembly 10 to the user (e.g., when the sensor assembly 10 is in the deployed state), the sensor assembly 10 is uncoupled from the sensor introducer 110 as shown in FIG. 9B. When uncoupled from the sensor introducer 110, the depressible region 13 and the switch contact 60 are no longer depressed and the switch contact 60 returns to a natural undepressed state. Movement of the switch contact 60 to its natural undepressed state causes the switch contact 60 to move out of contact with the first and second contact pads 68a, 86b to interrupt electrical continuity therebetween. In this state, the switch "S" is enabled such that the switch "S" triggers delivery of power from the battery 50 to the power control circuit 160. More specifically, enablement of the switch "S" triggers delivery of power from the battery 50 to the controller switch 164. The output of the controller switch 164 is latched by the power latch 162 for output to the power converter 166, which steps down the voltage of the controller switch 164 output to relatively lower voltages in accordance with the needs of the various components of the electrical subsystem 14. In some embodiments, enablement of the switch "S" need only be a momentarily input trigger signal since enablement of the switch "S" triggers the power latch 162 to maintain the output of the controller switch 164 to the power converter 166 such that the latched output of the power control circuit 160 serves to power one or more components of the electrical subsystem 14 indefinitely, even after the input signal from the switch "S" is removed. Thus, once the switch "S" is enabled, the switch contact 60 may contact the first and second contact pads 68a, 68b to establish electrical continuity therebetween without affecting the latched output of the controller switch 164. This state may remain indefinitely until the controller switch 164 is returned to a standby state (e.g., via application of an external signal to the controller switch 164).

Although the example of FIGS. 9A and 9B describes enabling of the switch "S" as being caused by opening of the switch "S" and/or interrupting of electrical continuity between the first and second contact pads 68a, 68b, in some embodiments, enabling of the switch "S" may be caused by closing of the switch "S" and/or establishing electrical continuity between the first and second contact pads 68a, 68b. In such embodiments, disabling of the switch "S" may be caused by opening of the switch "S" or by interrupting electrical continuity between the first and second contact pads 68a, 68b.

Although the example of FIGS. 9A and 9B depicts the switch contact 60; the protrusion 210; the depressible region 13; the battery contact pad 66; and the contact pads 68a and 68b as being disposed above the battery 50, in some embodiments, similar components may be disposed below the battery 50. For example, a protrusion (similar to the protrusion 210) may extend upward from the cover 114 such that when the cover 114 is removably coupled to the sensor introducer 110, the protrusion causes depression of a switch contact (similar to the switch contact 60). Accordingly, when the cover 114 is separated from the sensor introducer 110 prior to deployment, the switch contact 60 would no longer be depressed.

The embodiments disclosed herein are examples of the claimed subject matter, which may be embodied in various forms. For instance, although certain embodiments herein are separately described, it should be appreciated that each of the embodiments herein may be combined with one or more of the other embodiments described herein. Specific structural and functional details disclosed herein are not to be interpreted as limiting, but as a basis for the claims and as a representative basis for teaching one skilled in the art to variously employ the disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the disclosure. To the extent consistent, any or all of the aspects detailed herein may be used in conjunction with any or all of the other aspects detailed herein. Various alternatives and modifications can be devised by those skilled in the art without departing from the disclosure. Accordingly, the disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A sensor assembly for sensing a physiological characteristic, the sensor assembly comprising:
    a housing configured to be removably coupled to an introducer device for transitioning the sensor assembly from a pre-deployment state wherein the housing is coupled to the introducer device, to a deployed state wherein the housing is decoupled from the introducer device and deployed to a user;
    a depressible region disposed on the housing and configured to be depressed by the introducer device when the sensor assembly is in the pre-deployment state;
    a power source enclosed within the housing;
    a switch electrically coupled to the power source and configured to transition from a disabled state to an enabled state upon transition of the sensor assembly from the pre-deployment state to the deployed state, wherein the switch is configured to inhibit delivery of power from the power source to the sensor assembly when the switch is in the disabled state;
    a switch contact disposed within the housing between the depressible region and the power source, wherein the switch contact is configured to be:
        depressed by the depressible region when the sensor assembly is in the pre-deployment state to maintain the switch in the disabled state; and
        out of contact with the depressible region when the sensor assembly is in the deployed state to cause the switch to transition from the disabled state to the enabled state; and
    a power control switch coupled to the power source and configured to inhibit delivery of power from the power source to the sensor assembly when the switch is in the disabled state and, in response to the transition of the switch from the disabled state to the enabled state, maintain a latched output to one or more components of the sensor assembly while the sensor assembly is in the deployed state.

2. The sensor assembly according to claim 1, wherein transition of the switch from a closed state to an open state is configured to transition the switch from the disabled state to the enabled state.

3. The sensor assembly according to claim 1, wherein depression of the switch contact is configured to close the switch to place the switch in the disabled state.

4. The sensor assembly according to claim 1, further comprising a power converter coupled to the power control switch and configured to step down a voltage of the latched output of the power control switch for delivery of the latched output to the one or more components of the sensor assembly.

5. The sensor assembly according to claim 4, wherein the power converter is configured to consume a maximum of about 5 nA of current from the power source when the sensor assembly is in the pre-deployment state.

6. The sensor assembly according to claim 4, wherein the power converter is a step-down buck converter.

7. The sensor assembly according to claim 4, wherein the power converter is configured to consume a maximum of about 330 nA of quiescent current from the power source when the sensor assembly is in the pre-deployment state.

8. The sensor assembly according to claim 1, further comprising a power latch operably coupled to the power control switch and configured to latch an output of the power control switch to generate the latched output.

9. The sensor assembly according to claim 1, wherein the switch is configured to be maintained in the disabled state by the introducer device while the sensor assembly is in the pre-deployment state.

10. The sensor assembly according to claim 1, wherein the power control switch is configured to consume a maximum of about 20 nA of current from the power source when the sensor assembly is in the pre-deployment state.

11. The sensor assembly according to claim 1, wherein the power control switch is a pushbutton on/off controller.

12. The sensor assembly according to claim 1, further comprising a sensor extending from the housing for insertion into subcutaneous tissue of the user.

13. The sensor assembly according to claim 1, further comprising an antenna configured to enable communication between the sensor assembly and a handheld computing device.

14. The sensor assembly according to claim 1, wherein the power source is a lithium battery.

15. A sensor assembly for sensing a physiological characteristic, the sensor assembly comprising:
    a housing;
    a power source enclosed within the housing;
    a power control switch electrically coupled to the power source;
    a power latch configured to latch an output of the power control switch to generate a latched output for delivery to one or more components of the sensor assembly upon deployment of the sensor assembly to a user;
    a switch electrically coupled to the power source and configured to transition from a disabled state to an enabled state upon deployment of the sensor assembly to the user, wherein the power control switch is configured to inhibit consumption of power from the power source when the switch is in the disabled state and to facilitate consumption of the latched output in response to the transition of the switch from the disabled state to the enabled state; and
a switch contact disposed within the housing and configured to:
  be depressed when the sensor assembly is in a pre-deployment state to maintain the switch in the disabled state; and
  cause the switch to transition from the disabled state to the enabled state when the sensor assembly is in a deployed state.

16. The sensor assembly according to claim 15, wherein the power latch is configured to maintain consumption of the latched output indefinitely when the sensor assembly is deployed to the user.

17. The sensor assembly according to claim 15, further comprising a power converter coupled to the power control switch and configured to step down a voltage of the latched output of the power control switch.

18. A sensor assembly for sensing a physiological characteristic, the sensor assembly comprising:
  a housing configured to be removably coupled to an introducer device for transitioning the sensor assembly from a pre-deployment state wherein the housing is coupled to the introducer device, to a deployed state wherein the housing is decoupled from the introducer device and deployed to skin of a user;
  a power source enclosed within the housing;
  a power control switch coupled to the power source;
  a power latch configured to latch an output of the power control switch to generate a latched output; and
  a power converter coupled to the power control switch and configured to step down a voltage of the latched output of the power control switch for delivery of the latched output to one or more components of the sensor assembly, wherein the power control switch is configured to inhibit consumption of power from the power source when the sensor assembly is in the pre-deployment state and output the latched output to the power converter in response to transition of the sensor assembly from the pre-deployment state to the deployed state for delivery of the latched output to the one or more components of the sensor assembly.

19. The sensor assembly according to claim 18, further comprising a switch electrically coupled to the power source and configured to transition from a disabled state to an enabled state upon transition of the sensor assembly from the pre-deployment state to the deployed state, wherein the power control switch is configured to inhibit consumption of power from the power source when the switch is in the disabled state and output the latched output to the power converter in response to transition of the switch from the disabled state to the enabled state for delivery of the latched output to the one or more components of the sensor assembly.

20. The sensor assembly according to claim 18, wherein the power latch is configured to maintain delivery of the latched output to the one or more components of the sensor assembly indefinitely when the sensor assembly is in the deployed state.

* * * * *